US012768829B2

(12) United States Patent
Frischauf et al.

(10) Patent No.: US 12,768,829 B2
(45) Date of Patent: Oct. 20, 2026

(54) METHOD OF DETECTING THE PRESENCE OR ABSENCE OF A CLOT IN A LIQUID SAMPLE ANALYZER

(71) Applicant: Radiometer Medical ApS, Brønshøj (DK)

(72) Inventors: Peter Aage Frischauf, Broendby (DK); Michael Taagaard, Hoersholm (DK); Flemming Aas, Dyssegaard (DK)

(73) Assignee: Radiometer Medical ApS, Brønshøj (DK)

( * ) Notice: Subject to any disclaimer, the term of this patent is extended or adjusted under 35 U.S.C. 154(b) by 525 days.

(21) Appl. No.: 17/643,691

(22) Filed: Dec. 10, 2021

(65) Prior Publication Data

US 2022/0099656 A1 Mar. 31, 2022

Related U.S. Application Data

(63) Continuation of application No. 16/064,707, filed as application No. PCT/EP2016/081644 on Dec. 19, 2016, now Pat. No. 11,226,328.

(30) Foreign Application Priority Data

Dec. 22, 2015 (DK) ........................... PA 2015 00832

(51) Int. Cl.
*G01N 33/49* (2006.01)
*A61B 5/1495* (2006.01)
(Continued)

(52) U.S. Cl.
CPC ....... *G01N 33/4915* (2013.01); *A61B 5/1495* (2013.01); *G01N 33/492* (2013.01);
(Continued)

(58) Field of Classification Search
None
See application file for complete search history.

(56) References Cited

U.S. PATENT DOCUMENTS 5,571,396 A 11/1996 Cormier et al.
6,360,582 B1 3/2002 Chelvayohan et al.
(Continued)

FOREIGN PATENT DOCUMENTS

CN 102472719 5/2012
CN 104344864 2/2015
(Continued)

OTHER PUBLICATIONS

International Search Report for International Application No. PCT/EP2016/081644, Mar. 1, 2017.
Written Opinion of the International Search Authority of International Application No. PCT/EP2016/081644.

*Primary Examiner* — Brittany I Fisher
(74) *Attorney, Agent, or Firm* — FBT Gibbons LLP

(57) ABSTRACT

A method of detecting a clot in a measurement chamber (2) of a liquid sample analyzer (1), the liquid sample analyzer (1) comprising one or more analyte sensors (3, 4), each one of the one or more analyte sensors (3, 4) being arranged for measuring a physical parameter for a respective analyte in a liquid sample in the measurement chamber (2), wherein detection is performed after conclusion of a rinsing procedure with a primary solution (Cal2) having a pre-determined primary composition with a primary level of the analyte, the method comprising the steps of (a) at least partly filling the measurement chamber (2) with a secondary solution (Rinse/Cal1) having a pre-determined secondary composition with a respective secondary level for each of the analytes, wherein the respective secondary level is different from the respective primary level; (b) immediately after filling the measurement chamber (2) with the secondary solution (Rinse/Cal1), obtaining an initial measurement result by
(Continued)

each of the one or more analyte sensors (3, 4); (c) flushing the measurement chamber (2) with the secondary solution (Rinse/Cal1); (d) after a time delay with respect to the initial measurement result, obtaining a subsequent measurement result by each of the one or more analyte sensors (3, 4); (e) comparing the respective initial and subsequent measurement results; and (f) determining presence or absence of a clot in the measurement chamber based on the comparison.

18 Claims, 2 Drawing Sheets

(51) Int. Cl.
*G01N 27/416* (2006.01)
*G01N 33/487* (2006.01)

(52) U.S. Cl.
CPC ..... *G01N 33/4925* (2013.01); *G01N 27/4163* (2013.01); *G01N 33/4905* (2013.01)

(56) References Cited

U.S. PATENT DOCUMENTS

| | | | |
|---|---|---|---|
| 2011/0312002 A1 | 12/2011 | Taktak et al. | |
| 2012/0090993 A1 | 4/2012 | Mansouri et al. | |
| 2013/0292246 A1 | 11/2013 | Zelin et al. | |
| 2014/0221911 A1 | 8/2014 | Van Wieren et al. | |
| 2015/0323511 A1* | 11/2015 | Hendry ............. | G01N 33/0006 73/1.02 |

FOREIGN PATENT DOCUMENTS

| | | |
|---|---|---|
| EP | 2 275 808 A2 | 1/2011 |
| JP | 60-13254 | 1/1985 |
| JP | 2-57961 | 2/1990 |
| JP | 2005-501252 | 1/2005 |
| JP | 2015-522153 | 8/2015 |
| WO | WO 2004/040284 A1 | 5/2004 |
| WO | WO 2014/006406 A1 | 1/2014 |

* cited by examiner

METHOD OF DETECTING THE PRESENCE OR ABSENCE OF A CLOT IN A LIQUID SAMPLE ANALYZER

This application is a continuation of application Ser. No. 16/064,707, filed Jun. 21, 2018, which is a national stage filing under 35 U.S.C. § 371 of International Application No. PCT/EP2016/081644, filed on Dec. 19, 2016, which claims priority of Danish Patent Application No. PA 2015 00832, filed Dec. 22, 2015. The contents of these applications are each incorporated herein by reference.

The present invention relates in one aspect to a method of detecting a clot in a liquid sample analyzer comprising one or more analyte sensors for measuring a physical parameter for respective analytes, and to a liquid sample analyzer comprising a measuring chamber with one or more such analyte sensors, and a signal processor configured for detecting a clot in the measuring chamber.

In a particular aspect, the present invention relates to a method of detecting a clot in a blood analyzer comprising one or more analyte sensors for measuring blood parameters, and to a blood analyzer comprising a measuring chamber with one or more such analyte sensors, and a signal processor configured for detecting a clot in the measuring chamber.

According to a yet further aspect, a computer-implemented method of detecting a clot in a liquid sample analyzer, and a corresponding software product that can be loaded into a signal processor of a liquid sample analyzer are provided. Also in this aspect, the liquid sample analyzer may be a blood analyzer for analyzing e.g. a whole blood sample.

BACKGROUND OF THE INVENTION

Analyzers for measuring physical parameters of analytes in a liquid sample by means of respective analyte sensors are widely used in various industries, such as food industry, environmental industry, as well as medical and clinical industry. To ensure both accurate and precise results, the performance of such analyzers and the associated sensors is continuously scrutinized. This typically includes both detailed calibration and quality control procedures using standardized reference liquids including the respective analytes in well-defined compositions. The accurate and precise operation of analyzer systems is of particular importance in clinical analysis applications for analyzing physical parameters of analytes in bodily fluids, such as whole blood. In addition to the accuracy, precision, and reliability requirements, such analyzer systems for clinical applications are also subject to further critical constraints, such as a short time for obtaining a measurement result, and the capability of providing the highly reliable results from very small sample volumes.

The combination of all these constraints is particularly relevant in blood analyzers. Blood analyzers provide measurements of various parameters for analyzing the blood of a mammal subject, e.g. for establishing and/or monitoring a biological condition of the subject. Typically, the mammal subject is a human patient. In a variety of instances it is desirable to measure e.g. the partial pressure of blood gasses in a whole blood sample of the mammal subject, concentrations of electrolytes and metabolites in the blood sample, as well as the hematocrit value of the blood sample. For example, measuring pCO2, pO2, pH, Na+, K+, Ca2+, Cl−, glucose, lactate and hemoglobin values are primary clinical indications in assessing the condition of a medical patient. A number of different analyzers currently exist for making such measurements. Such analyzers are able to perform precise measurements in order to provide the most meaningful diagnostic information.

In order to use as little of the patient's blood as possible in each analysis performed, the measuring chamber which is employed to analyze a blood sample is preferably relatively small. Performing blood analysis using a small blood sample is important when a relatively large number of samples must be taken in a relatively short amount of time or if the volume of blood is limited, as in neonates. For example, patients in intensive care require a sampling frequency of 15-20 per day for blood gas and clinical chemistry measurements, leading to a potentially large loss of blood during patient assessment. Furthermore, in order to limit the number of tests which must be performed it is desirable to gather as much information as possible upon completion of each test. Furthermore, for the same reasons, it is important that the measurements and corresponding analysis results obtained from these measurements are reliable. Each measurement is therefore typically subject to a calibration and/or quality control procedure using different rinsing, calibration and/or reference liquids and the measurement chamber is thoroughly rinsed after each measurement to avoid contamination of any subsequent measurements.

However, a common issue in blood analyzers, in particular in systems with very small measurement chambers, is due to the presence of clots in whole blood samples. The clots may result in the formation of plugs impeding, obstructing or even completely blocking the fluid passages of the measurement chamber. Such clots may severely affect the measurements or even cause damage to the measurement chamber/sensor assembly. Known systems may therefore monitor the filling and discharge procedures for abnormalities in order to e.g. generate an alarm, stop the fluid handling infrastructure from feeding further fluid to the measurement chamber, and requesting a rinse and/or initiating an automated rinsing procedure. For example, the filling of the measurement chamber may be monitored by liquid sensors for detecting the passage of a liquid interface at an inlet upstream of the measurement and the corresponding subsequent occurrence of the liquid at an outlet downstream of the measurement chamber after an expected filling time. Unexpected behavior, e.g. expiry of the expected filling time without positive detection of the liquid interface at the outlet liquid sensor, may result in an alarm and/or initiation of a rinsing/maintenance procedure. Furthermore, by designing a simple flow path through the measurement chamber the formation of deposits can be counteracted and rinsing/washout can be facilitated.

While such strategies for detecting the presence of a clot in the measurement chamber are implemented and proof to be most helpful for a reliable operation of blood analyzer systems, it has been observed by the inventors that not all artifacts may be accounted for by these strategies and detection techniques.

Accordingly, it is a merit of the present invention to identify that further artifacts may arise due to clots, which are normally not detectable by the known clot detection routines that are based on flow behavior. Clots that do not noticeably affect the filling and discharge flow in the measurement chamber may nevertheless cause a severe distortion of the physical parameters of at least some of the analytes for a given sample, thus leading to erroneous analysis results. Therefore, there is a need for rapidly and reliably detecting any such additional causes of potential artifacts in blood analyzers in order to ensure accuracy and precision of the measurements and avoid the waste of valuable patient blood. Furthermore, such additional artifacts may also occur more generally in liquid sample analyzers. Accordingly, there is a further need for rapidly and reliably detecting any such additional causes of potential artifacts in liquid sample analyzers in order to ensure accuracy and precision of the measurements.

Object of the present invention is therefore to provide a method of detecting a clot contamination in a measurement chamber with improved sensitivity, and a system adapted to perform such clot detection method with improved sensitivity. According to a further aspect a further object is to provide a rapid clot detection technique that can be easily applied in an automated manner or upon request by a user that may yield a result within minutes or even less.

SUMMARY OF THE INVENTION

A first aspect of the invention relates to a method of detecting a clot in a measurement chamber of a liquid sample analyzer, the liquid sample analyzer comprising an analyte sensor being arranged for measuring a physical parameter of an analyte in a liquid sample in the measurement chamber, wherein detection is performed after conclusion of a rinsing procedure with a primary solution having a pre-determined primary composition with a primary level of the analyte, the method comprising the steps of: (a) removing the primary solution from the measurement chamber, and at least partly filling the measurement chamber with a secondary solution having a pre-determined secondary composition with a secondary level of analytes, wherein the secondary level is different from the primary level; (b) immediately after filling the measurement chamber with the secondary solution, obtaining an initial measurement result by the analyte sensor; (c) flushing the measurement chamber with the secondary solution; (d) after a time delay from obtaining the initial measurement result, obtaining a subsequent measurement result by the analyte sensor; (e) comparing the initial and subsequent measurement results; and (f) determining presence or absence of a clot in the measurement chamber based on the comparison.

The present invention is useful for the detection of a clot in the measurement chamber of a liquid sample analyzer, and further for verification of the presence of a suspected clot or after conclusion of measures for the removal of a previously detected clot. The detection result may be used as a part of the self-control routines, or may be requested by a user or otherwise be triggered externally; The detection result may further trigger an alarm or error state of the liquid sample analyzer, and may also be used to invoke a clot removal procedure and/or request external service, maintenance or replacement of the faulty measurement chamber if removal of the clot proofs unsuccessful.

A clot of the kind that becomes detectable by the present invention spoils the measurement by polluting the sample inside the measurement chamber. It should be noted that this is of particular relevance to liquid sample analyzers with very small sample volumes that are particularly susceptible to pollution, due to even minute amounts of parasitic analyte emitted from a clot, or due to minute amounts of actual analyte removed from the actual sample by absorption in the clot. The clot may be seen as a reservoir with a capacity for the uptake and emission of analyte, thereby causing pollution by acting as an analyte source or as an analyte sink whenever there is a gradient in the analyte concentration between the clot and the surrounding liquid sample.

The clot detection procedure may be conceived as determining a step-response of the measurement set-up to a "sudden switch" of the concentration level for respective analytes, which within applicable measurement tolerances is characteristic for a given set-up. Typically, at least a characteristic upper limit for the difference between the initial and subsequent measurement results may be derived, and may be used for deriving a reliable threshold for discriminating between a "normal behavior" without a clot in the measurement chamber and an "abnormal behavior" indicating the presence of a clot in the measurement chamber.

Advantageously, for a given configuration of a liquid sample analyzer with measurement chamber and associated sensors, such a threshold may be derived as a representative value for all liquid analyzers of the same type, and may be programmed as a fixed value. Alternatively or in addition thereto, the threshold value may be a user configurable setting of the liquid sample analyzer. Furthermore, a threshold may be dynamically determined in a self-learning calibration/initialization routine performed by the liquid analyzer, e.g. upon installation/replacement of a measurement assembly or sensor cassette in the analyzer.

Advantageously according to some embodiments, the stabilization response of the measurement set-up may be quantified and may be formulated e.g. as a dimensionless ratio of the difference in analyte levels between the initial and subsequent measurement sequences divided by the difference between the analyte levels in the primary and secondary solutions. The threshold for discriminating between "normal" and "abnormal" behavior may then be given as a corresponding percentage scaled to the difference in analyte levels between the primary and secondary solutions. A pollution response with a difference between the initial and subsequent analyte levels exceeding the threshold indicates the presence of a clot; whereas a pollution response below the threshold indicates a clearance, i.e. that no clot contamination is detectable in the measurement chamber.

A liquid sample analyzer may typically comprise a measurement chamber, one or more analyte sensors facing the measurement chamber, an analyzer part with a signal processor, and fluid handling infrastructure. The measurement chamber is adapted for receiving and containing a liquid sample to be analyzed with respect to a number of different analytes. The sensor surfaces facing the measurement chamber are selectively sensitive to respective analytes and are adapted to generate corresponding signals. The signal processor communicates with the sensors for collecting and processing the signals. In "normal" operation, the user may provide a liquid sample at an input port of the analyzer. The liquid sample is transferred to the measurement chamber comprising the sensors. The measurement chamber may be equipped with a plurality of analyte sensors arranged to provide essentially simultaneous measurements on analyte parameters in a liquid sample, e.g. a whole blood sample, wherein preferably the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in the European patent EP 2 147 307 B1. Details of a suitable sensor design that may be used for blood and body fluid parameter analysis in a liquid sample analyzer are also found in literature. For example, EP 2 361 380 B1 discloses a planar sensor determining the partial pressure of $CO_2$ of a blood sample, and U.S. Pat. No. 6,805,781 B2 discloses a sensor with an ion-selective electrode device using a solid state, inner reference system. Following pre-programmed routines, measurements are performed using the analyte sensors. In order to obtain a measurement sequence from an analyte sensor for the respective analyte, a series of values attributable to the physical parameter measured by the sensor is recorded subsequently one after the other at respective times.

The analyte sensors generate signals representative of a physical parameter for the respective analyte and provide the signals to the analyzer part. The analyzer part comprises a signal processor that is adapted to receive and process signals from the analyte sensors, and present the processed signals as output to a user or to a subsequent/further data analysis. After measurement, the liquid sample is discharged, and the measurement chamber is prepared for the next measurement. Performing the measurements, calibration tasks, and quality control procedures thus typically involves the loading, unloading, rinsing, cleaning and reloading of different liquids, which may be done by the fluid handling infrastructure. Fluid handling may be manual, partly automated or fully automated depending on the system. The fluid handling infrastructure may comprise a kit with process solutions of known compositions, such as comprising those solutions listed in Table 1 below. Advantageously, the signal processor may further be adapted to communicate with the fluid handling infrastructure for controlling fluid flow to and from the measurement chamber, e.g. for filling, flushing or discharging a user sample and any of the process solutions in an automated or at least semiautomated manner. The analyzer may perform self-control routines including calibration and quality control. An example of a method for performing calibration and quality control of a sensor in a liquid sample analyzer in a cyclic manner is described for example in U.S. Pat. No. 7,338,802 B2. Most advantageously, the analyzer is further programed to maintain the measurement chamber and the associated sensors in a well-defined electrochemical idle state and to continuously monitor the status of the analyzer in general and of the sensor status in particular. If any abnormality is detected, the analyzer may indicate the deviation to a user, and may further initiate measures or indicate ways of overcoming an error state. Advantageously, the well-defined idle state includes keeping a standard idle state solution in the measurement chamber and in contact with the sensitive surfaces of the sensors facing the chamber. A suitable example for such a standard idle state solution is also given below in Table 1, labelled RINSE/CAL1 (S1920).

An important and distinguishing advantage is that the present invention uses actual analyte measurements performed inside the measurement chamber to detect a clot. In fact, the invention may most advantageously be performed using signals from the very analyte sensors that would be affected by the presence of a clot in the measurement chamber. The high reliability of the clot detection according to the present invention is amongst others achieved, due to the fact that the presence of a clot is determined directly from the characteristics of the mechanism, which is the root cause of the artefacts that the clot would also introduce in a measurement on a valuable user sample.

The clot detection has a fast cycle time occupying the liquid sample for only what corresponds to a simple measurement on a sample, after which the liquid sample analyzer is again available for measurements—unless a clot has been detected. However, also in this case the rapid detection/verification of the presence of a clot in the measurement chamber avoids erroneous measurement results and waste of valuable samples. The rapid procedure for determining presence or absence of a clot also encourages a user to perform such a clot procedure as a precautionary measure, e.g. in order to eliminate this potential source of measurement error before feeding a particularly valuable sample to the apparatus. The method of the invention therefore has the further advantage that it is particularly effective in rapidly catching any faulty status caused by a clot as soon as the presence of a clot in the measurement chamber is suspected. In case a clot has been detected measures for its removal may be taken, and the rapid clot detection techniques according to the present invention are again useful for verifying the removal of the clot from the measurement chamber. Further advantageously, the procedure may be useful for implementation as part of a regular maintenance and/or quality control routine, thus allowing for catching the fault as soon as it occurs by continued/programmed routine checks.

The presence or absence of a clot in the measurement chamber may equally be determined by characterizing the response to switching from a high analyte level in the primary solution to a low analyte level in the secondary solution; or the clot detection procedure may be equally performed by characterizing the response to switching from a low primary analyte level to a high secondary analyte level. Advantageously, the clot detection procedure is performed starting in an idle state of the liquid sample analyzer, by switching from a "standard" idle solution present in the measurement to a different known solution and back, wherein the initial and subsequent measurement results for clot detection are actually collected on the standard idle solution, in response to the switch-back from the different known solution acting as primary solution to the standard idle solution acting as secondary solution. The different known solution is therefore only in the measurement chamber for a relatively short time, just enough to properly imbibe a potential clot with analytes at the level of the different known solution. This has amongst other the advantage of more quickly returning to the idle state, and minimizing the exposure of the measurement chamber and the sensor surfaces to a fluid that is different from the standard idle solution. Thereby it is achieved, that the liquid sample analyzer more rapidly can return to an operational state ready for performing a new measurement on a sample.

The same and further advantages are also achieved in an analogous way by the further embodiments and the further aspects of the invention as defined in the following.

Further according to some embodiments of the method, presence of a clot is determined if the difference between the respective initial and corresponding subsequent measurement results is above a respective threshold for at least one of the one or more analyte sensors, and/or absence of a clot is determined if the difference between the respective initial and corresponding subsequent measurement results is below the respective threshold for all of the one or more analyte sensors. This allows for a simple implementation of the discrimination criterion for determining presence and/or absence of a clot that would cause artefacts significantly affecting the measurement results on a user sample. The threshold may be determined in any suitable manner, e.g. by observing over a longer period of operation a "normal" behavior, where the measurement chamber is clearly free of clots affecting the accuracy and precision of the analysis results and deriving a threshold from that observation. Based on a characteristic value for the difference between the initial and subsequent results under normal operation conditions, i.e. in the absence of a clot, a threshold value may be derived. For example, a threshold of two or three times the characteristic value may be selected. Presence of a clot may be determined, if only one of the analyte sensors exceeds a respective threshold, thereby indicating an abnormal behavior. The criterion of determining absence of a clot is complementary to the above criterion for determining presence of a clot. Absence of a clot may be determined, e.g. if all of the analyte sensors included in the detection procedure stay below their respective threshold, thereby indicating a normal behavior. The thresholds may be pre-determined, with respective values for each of the analyte sensors. According to some embodiments, for the sake of simplicity, a common threshold value that is the same for all analyte sensors may be determined. Preferably, the common threshold value or the respective threshold values are the same for determining presence and absence of a clot to avoid potential ambiguities.

Further according to some embodiments of the method, the liquid sample analyzer system is a blood analyzer system. The present invention is particularly useful for implementation in a blood analyzer, where the requirements for clinically acceptable measurement precision and accuracy are extremely challenging and where measurement chamber volumes may be in the microliter regime, thereby catching many of the fault issues related to the presence of clots introduced by sample taking, resulting from fibrinogen clot formation, or the like, at an early stage.

Further according to some embodiments of the method, the analyte sensors are one or more of dedicated sensors for measuring partial pressures of gasses, concentrations of electrolytes, concentrations of metabolites, concentrations of nutritional and/or pharmaceutical substances, and pH.

Further according to some embodiments of the method, the one or more analytes are one or more of Na+, K+, Ca2+, Mg2+, Cl−, glucose, lactate, urea, creatinine, CO2, and 02.

Advantageously according to some embodiments, a plurality of analyte sensors is included in the clot detection routine, thereby increasing reliability of the detection result, and, if different types of sensors and/or sensors selective to different analytes are employed, a broader range of clots may be detectable, such as clots that might only affect some analyte sensors but not others, or clots that might selectively pollute some analyte measurements, but not others. Further advantageously according to some embodiments, the analyte sensors are located at different locations distributed along the measurement chamber. Advantageously, the different locations are distributed along a flow path from an inlet port to an outlet port of the measurement chamber over essentially the entire length of that flow path, or at least 70%, or at least 50%, or at least 30%, or between 60% and 90%, or between 40% and 60% of the length of that flow path. By including measurements in the clot detection procedure that have been obtained from sensors that are spaced apart from each other, at different locations distributed within the measurement chamber, the measurement chamber is more reliable probed.

Further according to some embodiments of the method, the one or more analyte sensors are selected from the group of electrochemical sensors and optical sensors. The method is particularly useful for detecting clots that may directly affect the signal generated by the sensors, e.g. due to a polluted clot acting on the sensor mechanism. This may e.g. be the case, if a clot is deposited on top of an electrochemical electrode device where the actual potential seen by the electrode device may be directly affected by the clot. The method is therefore particularly useful for detecting clots where electrochemical sensors are used, such as in a blood analyzer. However, since a clot that is present in a measurement chamber actually may pollute the liquid sample that is to be measured, any type of analyte sensor that is sensitive to a change in analyte level, such as optical sensors, may be exploited to determine the presence or absence of a clot using the invention.

Further according to some embodiments of the method, at least one electrochemical analyte sensor includes an ion selective electrode. As also mentioned above, electrochemical electrode devices may be affected directly by a clot deposited at least partially over the sensitive area of the sensor facing the measurement chamber. This may be even more an issue for ion selective electrode devices, such as those used in blood analyzers. The method is therefore particularly useful for electrode devices of this type.

Further according to some embodiments of the method, obtaining the one or more respective initial and/or corresponding subsequent measurement results includes developing an initial measurement result from a respective initial measurement sequence and/or developing a subsequent measurement result from a corresponding subsequent measurement sequence. By including a measurement sequence for obtaining the initial and/or the subsequent measurement results, more reliable values may be achieved. By basing the comparison for determining presence or absence of a clot on a comparison of initial and subsequent measurement results of increased reliability, the discrimination between presence and absence of a clot becomes more stable.

Further according to some embodiments of the method, the initial measurement result is an average over the respective initial measurement sequence and/or wherein the subsequent measurement result is an average over the corresponding subsequent measurement. In cases where the duration of taking a measurement sequence covers a period, where the underlying signal generated by the analyte sensor may be considered as essentially constant averaging is particularly effective way of improving a signal-to-noise ratio and obtaining a reliable measurement result for the discrimination.

Further according to some embodiments of the method, the initial measurement result is an initial rate of change for the initial measurement sequence, and wherein the subsequent measurement result is a subsequent rate of change for the corresponding subsequent measurement sequence. In some cases it may be conceived that the duration of taking a measurement sequence covers a period, where the underlying signal generated by the analyte sensor, in particular for the initial measurement has not as yet stabilized and evidently evolves towards a stabilized state. In such a case, obtaining the measurement results as a rate of change may be the most appropriate way of obtaining a reliable measurement result for the discrimination. A rate of change may e.g. be obtained by regression to the respective measurement sequence.

Further according to some embodiments of the method, the level of the one or more analytes contained in the primary and secondary solutions differs by at least a factor of 2, at least a factor of 5, at least a factor of 10, at least a factor of 20, at least a factor of 50, or at least a factor of 100. A larger difference in analyte level between the primary and secondary solutions, improves the sensitivity to even small pollution contributions from a potential clot, thereby improving detection sensitivity. A disadvantage of a particularly high concentration in one of the solutions is that it may strongly affect the electrochemical environment inside the measurement chamber, which may result in a longer recovery time or even in a permanent drift of the analyte sensors from the clot detection procedure. Generally, the primary and secondary analyte levels are only required to differ from each other, i.e. the primary analyte level may be larger than the secondary analyte level or vice versa. Also, generally, one of the primary and secondary analyte levels may be nominally zero within detection tolerances, but not both, in order to be useful for a clot detection procedure according to the invention.

Further according to some embodiments of the method, the level of the one or more analytes contained in the primary solution is larger than the level of the one or more analytes contained in the secondary solutions by at least a factor of 2, at least a factor of 5, at least a factor of 10, at least a factor of 20, at least a factor of 50, or at least a factor of 100. As described above, it may be advantageous that the primary solution is only introduced for a short period sufficient to imbibe a potentially present clot with the analyte at a level corresponding to that of the primary solution, wherein the primary solution differs from a standard idle solution, and then observe and characterize the response to a switch back to the standard idle solution as the secondary solution. Preferably the analyte levels in the standard idle solution are moderate, or more preferably low, in order to avoid a corruption of the sensitivity of the analyte sensors. Such embodiments are examples, where it may be particularly useful to have a primary analyte level that is larger than the secondary solution.

According to a further aspect, a method for verifying successful/unsuccessful removal of a clot previously identified in the measurement chamber is provided, the method comprising: performing the clot detection method according to any of the preceding claims after the presence of a clot in the measurement chamber has been determined, and after completion of measures intended for removal of said clot, the measures of clot removal concluding with a rinsing procedure using the primary solution. Further according to some embodiments, this method of verifying removal of a clot prior to the steps of the clot detection method comprises determining presence of a clot; and applying measures for removal of the clot. The above described method of detecting a clot is fast and therefore particularly useful for providing a rapid and reliable feedback on clot removal measures.

A further aspect of the invention relates to a liquid sample analyzer that is adapted for performing a method of clot detection according to any of the preceding claims, the liquid sample analyzer comprising a measurement chamber with inlet and outlet ports for feeding and discharging a liquid sample to the measurement chamber, one or more analyte sensors facing the measurement chamber, each of the one or more analyte sensors being arranged for measuring a physical parameter for a respective analyte in a liquid sample in the measurement chamber, and a signal processor configured for receiving signals from the one or more analyte sensors as an input, for performing a comparison of respective initial and corresponding subsequent measurements based on that input, and for determining presence or absence of a clot in the measurement chamber based on the comparison. By including a signal processor, which is configured to control the liquid sample analyzer to perform the steps for detecting a clot as described herein, the same advantages as achieved by the method according to any of the embodiments of the invention are implemented in a liquid sample analyzer.

Further according to some embodiments, the liquid sample analyzer is adapted for the measurement of blood parameters in whole blood samples. The present invention is particularly useful for implementation in a blood analyzer, where the requirements for clinically acceptable measurement precision and accuracy are extremely challenging, and where sample volumes are typically very small.

A further aspect of the invention relates to a computer-implemented method of detecting a clot in a measurement chamber of a liquid sample analyzer comprising one or more analyte sensors, the one or more analyte sensors being arranged for measuring a physical parameter for a respective analyte in a liquid sample in the measurement chamber, the method comprising the steps of:

- receiving initial measurement data obtained by the analyte sensor after conclusion of a rinsing procedure with a primary solution having a pre-determined primary composition with a primary level of the analyte, and immediately after replacing the primary solution in the measurement chamber with a secondary solution having a pre-determined secondary composition with a secondary level of the analyte different from the primary level;
- receiving subsequent measurement data obtained by the analyte sensor after flushing the measurement chamber with the secondary solution and after a time delay with respect to the initial measurement;
- comparing the initial and subsequent measurement data; and
- determining presence or absence of a clot in the measurement chamber based on the comparison.

Thereby the analogue advantages as discussed above with respect to the method and apparatus according to the invention are achieved. In addition thereto this allows implementing the method of the invention in a signal processor of a liquid sample analyzer, such as in particular a blood analyzer.

A further aspect of the invention relates to a software product that can be loaded to a signal processor of a liquid sample analyzer, the signal processor being configured for communicating with one or more analyte sensors facing a measurement chamber of the liquid analyzer, wherein the signal processor is further configured for communicating with a fluid handling system adapted for feeding and discharging liquid samples to the measurement chamber of the liquid analyzer, the software product comprising instructions for:

(i) performing a rinsing procedure with a primary solution;
(ii) replacing the primary solution with a secondary solution having a different composition than the primary solution;
(iii) immediately after filling the measurement chamber with the secondary solution, collecting from the one or more analyte sensors respective initial measurement data;
(iv) flushing the measurement chamber with the secondary solution;
(v) after a time delay with respect to collecting the initial measurement data, collecting from the one or more analyte sensors corresponding subsequent measurement data;
(vi) performing a comparison of the respective initial and corresponding subsequent measurement data; and
(vii) determining presence or absence of a clot in the measurement chamber based on the comparison.

The software product is useful for configuring the signal processor of a liquid sample analyzer for performing the method of determining the presence of a clot in a measurement chamber of the liquid sample analyzer comprising one or more analyte sensors, the one or more analyte sensors being arranged for measuring a physical parameter for a respective analyte in a liquid sample in the measurement chamber. The software product may even be used to upgrade existing liquid sample analyzers to include a clot detection procedure according to the invention in the toolbox of the liquid analyzer, e.g. for improving the self-control, calibration, and/or quality control procedures. By such an upgrade, an existing liquid analyzer may be improved to provide more reliable, more accurate and/or more precise measurement results. This is of particular importance for apparatus used in a clinical environment, where reliable, accurate and precise measurements are of the utmost importance, yet avoiding a costly replacement of the apparatus.

BRIEF DESCRIPTION OF THE DRAWINGS

Preferred embodiments of the invention will be described in more detail in connection with the appended drawings, which show in FIG. 1 a diagram of a blood analyzer according to one embodiment, FIG. 2 a schematic graph illustrating the signal of an analyte sensor for a respective analyte as a function of time during a clot detection procedure according to one embodiment of the invention, and in FIG. 3 a schematic graph illustrating the signal of an analyte sensor for a respective analyte as a function of time during a further clot detection procedure according to the same embodiment of the invention.

DETAILED DESCRIPTION OF PREFERRED EMBODIMENTS

Figure 1:
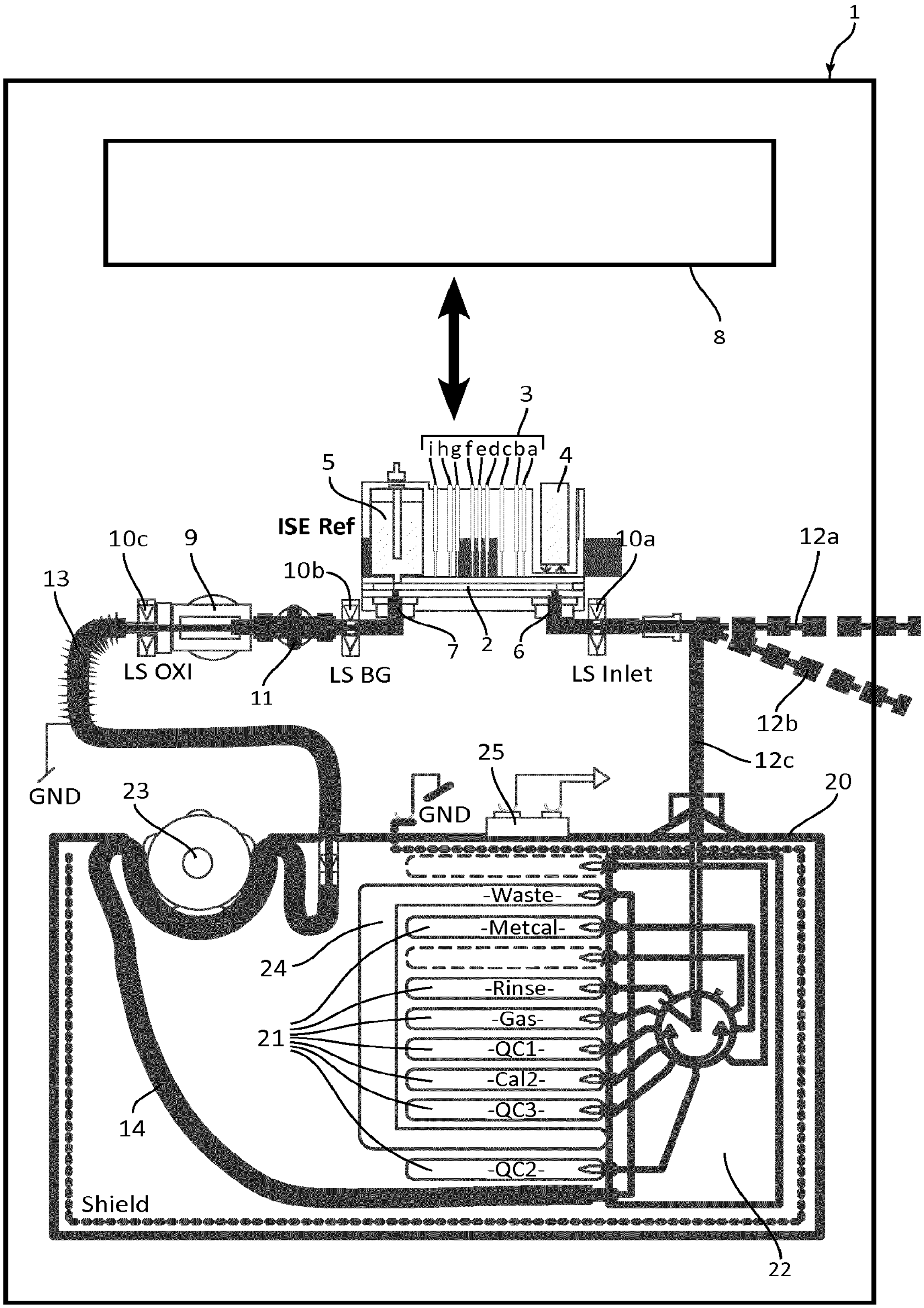

FIG. 1 shows schematically a liquid sample analyzer 1 with an analyzer part having a signal processor 8, one or more analyte sensors 3(*a-i*), 4, a measurement chamber 2, and fluid handling infrastructure 20. For performing measurements, the user may provide a liquid sample at an input port 12*a/b* of the analyzer 1. The liquid sample is transferred through an inlet port 6 to the measurement chamber 2 comprising a plurality of analyte sensors 3, 4. The analyte sensors 3, 4 are arranged to provide essentially simultaneous measurements on analyte parameters in a liquid sample, e.g. a whole blood sample. Preferably, the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 B1. Following pre-programmed instructions loaded in a signal processor 8 and/or user input, measurements are performed using the analyte sensors 3, 4. The analyte sensors 3, 4 generate signals that are representative of a physical parameter for the respective analyte and provide the signals to the signal processor 8 of the analyzer part. The signal processor 8 is adapted to receive and process signals from the analyte sensors 3, 4, and present the processed signals as output to a user or to a subsequent/further data analysis. After measurement, the liquid sample is discharged, and the measurement chamber 2 is prepared for the next measurement. The embodiment of the analyzer shown in FIG. 1 is particularly adapted for the measurement of blood parameters, and further comprises an optional oximetry measurement device 9 downstream of the measurement chamber 2. Performing the measurements, calibration tasks, and quality control procedures thus typically involves the loading, unloading, rinsing, cleaning and reloading of different liquids, which may be done by the fluid handling infrastructure 20. The fluid handling may be controlled in an automated way by the signal processor 8 according to pre-programmed instructions and/or user input. The fluid handling infrastructure 20 includes a number of reservoirs 21 pre-filled with process liquids (RINSE/CAL1, CAL2, QC1, QC2, Metcal) for rinsing/wash-out, calibration and quality control tasks. The process liquids (RINSE/CAL1, CAL2, QC1, QC2, Metcal) have a known composition. The exact composition of a given batch may be stored in a chip 25 that may be attached to a cassette comprising the reservoirs 21, wherein the chip 25 may be read by the signal processor 8. The process liquid (RINSE/CAL1, CAL2, QC1, QC2, Metcal) for a given process step may be selected by a fluid selector valve 22, and via feed line 12*c* transferred through the inlet port 6 to the measurement chamber 2. Correct filling of the measurement chamber 2 may be monitored and verified by visual inspection or according to known procedures by observing the propagation of a liquid interface through the system by means of liquid sensors 10*a*, 10*b*, 10*c* located upstream and downstream of the measurement chamber, such as at the inlet 6 ("LS inlet" 10*a*), at the outlet 7 ("LS BG" 10*b*), and just after the oximetry measurement device 9 ("LS OXI" 10*c*), respectively. The fluid flow through the analyzer is driven by a pump 23, here a peristaltic hose-pump arranged downstream of the measurement chamber 2 and the oximetry measurement device 9 and connected thereto via fluid line 13. The discharged fluids are finally transported through fluid line 14 to the waste reservoir 24.

By way of example, a kit of process fluids may include the following compositions with approximate concentrations of different substances contained in these compositions as given in Table 1 below.

TABLE 1

| | | Concentration | | |
|---|---|---|---|---|
| Substance | Unit | RINSE/CAL1 S1920 | CAL2 S1930 | Metcal S1940 |
| pH | | 7.30 | 6.8 | NA |
| $pCO_2$ | mmHg | 35 | NA | 80 |
| $pO_2$ | mmHg | 180 | NA | NA |
| $cNa^+$ | mmol/L | 150 | 70 | NA |
| $cK^+$ | mmol/L | 4 | 10 | NA |
| $cCl^-$ | mmol/L | 95 | 50 | NA |
| $cCa^{2+}$ | mmol/L | 0.5 | 2.3 | NA |
| cGlu | mmol/L | 0 | NA | 10 |
| cLac | mmol/L | 0 | NA | 10 |
| ctHb | g/dL | NA | NA | 0 |

Upon start-up and, in an ongoing manner, during uptime, the analyzer 1 performs self-control routines. If any abnormality is detected, the analyzer 1 indicates the deviation to a user, and may further indicate ways of overcoming an error state. On the other hand, when the analyzer indicates normal operation, measurements can be performed immediately. Advantageously according to some embodiments, the self-control routines may be performed during idle times, i.e. when the analyzer is in an idle state, where it is not used for performing actual measurements on a sample. The self-control control routines may include continued repetitive measurements performed on a calibration-grade process liquid with a precisely known composition, as e.g. stored on chip 25. A suitable liquid is for example the process liquid RINSE/CAL1, labelled S1920 in the Table 1. The signals obtained for each of the different analyte sensors on the well-known composition may then be used to continuously update the reference for the respective analyte measurements. By choosing a well-specified idle state solution for the continued idle state measurements it is also ensured that the ion-selective sensors are always in a well-defined electrochemical state, ready for performing a measurement on a user sample.

As explained, the presence of a clot may act as a reservoir for the uptake of analytes from a sample, or re-emission of previously absorbed analytes into the sample, thereby distorting the result of a measurement on a given liquid sample. The present invention is useful for the detection of clots in the measurement chamber of a liquid sample analyzer, and further for verification of the presence of a suspected clot or after conclusion of measures for the removal of a previously detected clot. The detection result may be used as a part of the self-control routines, or may be requested by a user or otherwise be triggered externally; The detection result may further trigger an alarm or error state of the liquid sample analyzer, and may also be used to invoke a clot removal procedure and/or request external service, maintenance or replacement of the faulty measurement chamber if removal of the clot proofs unsuccessful.

Figure 2:
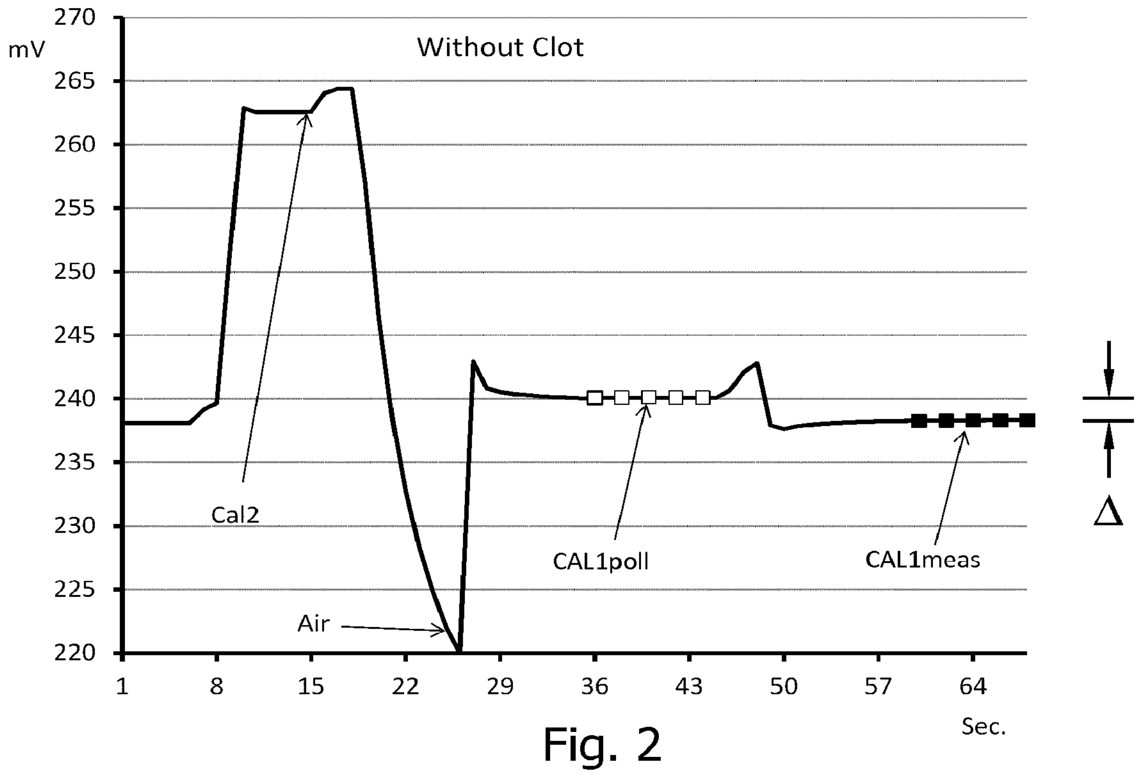
Figure 3:
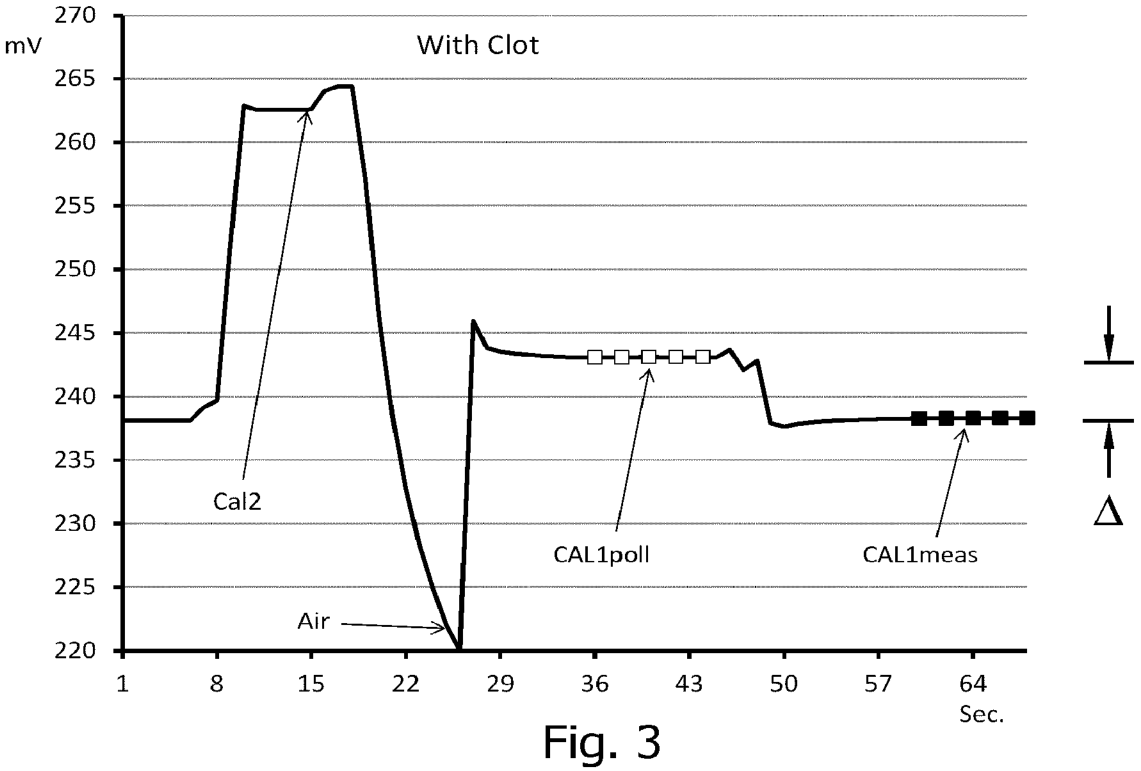

FIGS. 2 and 3 show schematic graphs illustrating the sensor signal of an analyte sensor during the course of one embodiment of a detection procedure, wherein FIG. 2 illustrates a potential trace for a single $K^+$ ion selective sensor as observed in the absence of a clot, and wherein FIG. 3 illustrates the corresponding curve as it may be observed in the case of a clot present in the measurement chamber of a liquid analyzer. In both FIGS. 2 and 3 the same fluid handling program is followed and the voltage output of the analyte sensor is recorded. As further explained in the following, the presence or absence of a clot can be detected from the difference of the traces, wherein the level of the ion concentration as seen by the analyte sensor between t=30 s and t=45 s is higher in the case of the presence of a clot as compared to the case of no clot being present in the measurement chamber. In FIGS. 2 and 3, the difference is schematically emphasized by the arrows labelled "A" on the right side of the graphs. Corresponding traces may also be recorded for other analyte sensors in the measurement chamber, and may be used analogously for detecting a clot either when taken alone or, if applicable, in combination with any of the other analyte sensors.

Following the traces of FIGS. 2 and 3 as a function of time, the following fluid handling sequence is performed together with the collection of the measurement data relevant to the clot detection. At the beginning of the traces, the analyzer is still in an idle state where the measurement chamber is filled with the rinsing solution "RINSE/CAL1" of table 1 above. The clot detection procedure starts at t=8 s, where a pump (e.g. pump 23 of FIG. 1) is activated for replacing the rinsing solution (RINSE/CAL1) by another known solution, "CAL2" of table 1 above, which here is used as the primary solution. The pump is operated to ensure filling the measurement chamber with the primary solution. In the example given here, about 100 μl of primary solution are used for a measurement set-up that is configured for a measurement chamber filling volume of 70 μl when measuring on a sample. As seen on the signal trace between t=10 s and t=15 s, the primary solution (CAL2) yields a higher signal from the analyte sensor, corresponding to a higher concentration of the respective analyte than the rinsing solution (RINSE/CAL1), which is used as a secondary solution. After filling has completed the pump is stopped for a settling time to allow for a stabilization of the primary solution fluid sample in the measurement chamber, before the pump again is activated to empty the measurement chamber at about t=20 s. After the measurement chamber has been emptied, the measurement chamber is filled again with the rinsing solution RINSE/CAL1, which is used as the secondary solution. When replacing the primary solution with the secondary solution care is taken to avoid mixing the two fluid fluids in order to ensure a reliable clot detection result. This may typically be achieved by avoiding a direct fluid interface between the two solutions, e.g. by separating the primary solution and the secondary solution by air. Furthermore, the filling amount of the secondary solution for replacing the primary solution is metered to just fill the measurement chamber rather than to completely flush the chamber with the secondary solution. In the present example, this amounts to about 70 μl of the secondary solution being transferred into the measurement chamber. Thereby the pollution effect of a clot, if present, on the analyte concentration of the secondary solution is maximized. The secondary solution (RINSE/CAL1) is again allowed to settle for stabilization in the measurement chamber, before an initial analyte level (CAL1poll) is determined as the average of an initial sequence of measurement results (open squares on FIG. 2) collected for the polluted state between t=35 s and t=45 s. After the initial measurement sequence has been taken, the pump is again operated, now in order to flush the measurement chamber with the secondary solution (RINSE/CAL1). In the present example, this amounts to at least 150 μl of the rinsing solution (RINSE/CAL1) being passed through the measurement chamber. The pump is again stopped to allow the secondary solution (RINSE/CAL1) in the measurement chamber to settle during a time delay, before a subsequent analyte level (CAL1meas) is determined as the average of a subsequent series of measurement results (filled squares on FIG. 2) that is collected by the signal processor after t=60 s. A slight difference in analyte levels between the initial and subsequent measurement sequences is typically observed and may e.g. reflect a characteristic stabilization response of the measurement chamber/sensor set-up when switching from one composition to another.

The above procedure may be conceived as determining a step-response of the measurement set-up to a "sudden switch" of the concentration level for respective analytes, which within applicable measurement tolerances is characteristic for a given set-up. Indeed, at least a characteristic upper limit for the difference between the initial and subsequent measurement results may be derived, and may be used for deriving a threshold for discriminating between a "normal behavior" without a clot in the measurement chamber and an "abnormal behavior" indicating the presence of a clot in the measurement chamber. For a given configuration of a liquid sample analyzer with measurement chamber and associated sensors, such a threshold may be derived as a representative value for all liquid analyzers of the same type, and may be programmed as a fixed value. Alternatively or in addition thereto, the threshold value may be a user configurable setting of the liquid sample analyzer. Furthermore, a threshold may be dynamically determined in a self-learning calibration/initialization routine performed by the liquid analyzer, e.g. upon installation/replacement of a measurement assembly or sensor cassette in the analyzer.

The stabilization response of the measurement set-up may be quantified and formulated e.g. as a dimensionless ratio of the difference in analyte levels (CAL1poll, CAL1meas) between the initial and subsequent measurement sequences over the difference between the analyte levels in the primary and secondary solutions: D=(CAL1meas−CAL1poll)/

(CAL2−CAL1meas); wherein CAL1meas and CAL1poll are measured, e.g. as described above, and wherein CAL2 may be the nominal or calibrated analyte level of the known primary solution, or may also be measured when the primary solution (CAL2) is present in the chamber. The threshold for discriminating between "normal" and "abnormal" behavior may then be given as a corresponding percentage scaled to the difference in analyte levels between the primary and secondary solutions. A pollution response with a difference between the initial and subsequent analyte levels exceeding the threshold indicates the presence of a clot; whereas a pollution response below the threshold indicates a clearance, i.e. that no clot contamination is detectable in the measurement chamber.

In the example given in FIGS. 2 and 3, a threshold of Dt=5% has been chosen. In FIG. 2, the initial and subsequent analyte levels (CAL1poll, CAL1meas) differ by 3% indicating that no clot is detected in the measurement chamber. In FIG. 3, the initial and subsequent analyte levels (CAL1poll, CAL1meas) differ by 8% indicating that a clot is detected in the measurement chamber.

Note that in the example given here the clot detection procedure is performed by characterizing the response to a switching from a higher primary analyte level to a lower secondary analyte level. In analogy thereto, the presence or absence of a clot in the measurement chamber may also be determined by characterizing the response to switching from a low analyte level in the primary solution to a high analyte level in the secondary solution.

However, in the above-described procedure, a switching from a "standard" idle solution (RINSE/CAL1) to a different known solution (CAL2 acting as primary solution) and back is performed, and the clot detection measurement sequences CAL1poll and CAL1meas are actually collected on the standard idle solution (RINSE/CAL1 acting as secondary solution), in response to the switch-back from the different known solution to the standard idle solution (RINSE/CAL1). The different known solution (CAL2) is therefore only in the measurement chamber for a relatively short time, just enough to properly imbibe a potential clot with analytes at the level of the different known solution (CAL2). This has amongst other the advantage of more quickly returning to the idle state, and minimizing the exposure of the measurement chamber and the sensor surfaces to a fluid that is different from the standard idle solution. Thereby it is achieved, that the liquid sample analyzer more rapidly can return to an operational state ready for performing a new measurement on a sample.

The invention claimed is:

1. A method of detecting a clot in a measurement chamber of a liquid sample analyzer, the liquid sample analyzer comprising one or more analyte sensors arranged for measuring a physical parameter of an analyte in a liquid sample in the measurement chamber, wherein detection is performed after conclusion of a rinsing procedure with a primary solution having a pre-determined primary composition with a primary concentration of the analyte, the method comprising:

(a) removing the primary solution from the measurement chamber and then at least partly filling the measurement chamber with a filling amount of a secondary solution having a pre-determined secondary composition with a secondary concentration of the analyte, wherein the filling amount of the secondary solution is metered to just fill the measurement chamber rather than to completely flush the measurement chamber with the secondary solution, wherein the secondary concentration is different from the primary concentration;

(b) obtaining an initial measurement result by at least one of the one or more analyte sensors;

(c) flushing the measurement chamber with the secondary solution, and leaving the secondary solution in the measurement chamber; and (d) after a time delay from obtaining the initial measurement result, obtaining a subsequent measurement result by at least one of the one or more analyte sensors.

2. The method according to claim 1, wherein the liquid sample analyzer is a blood analyzer system.

3. The method according to claim 1, wherein the measurement chamber comprises several analyte sensors for measuring different analytes.

4. The method according to claim 3, wherein the analyte sensors include one or more dedicated sensors configured for respectively measuring one or more of: partial pressures of gasses, concentrations of electrolytes, concentrations of metabolites, concentrations of nutritional or pharmaceutical substances, or pH.

5. The method according to claim 1, wherein the analyte is one or more of: $Na^+$, $K^+$, $Ca^{2+}$, $Mg^{2+}$, $Cl^-$, glucose, lactate, urea, creatinine, $CO_2$, or $O_2$.

6. The method according to claim 5, wherein at least one of the one or more analyte sensors is an electrochemical analyte sensor including an ion selective electrode.

7. The method according to claim 1, wherein the one or more analyte sensors are selected from the group consisting of electrochemical sensors and optical sensors.

8. The method according to claim 1, wherein obtaining the respective initial and/or corresponding subsequent measurement results includes developing the initial measurement result from a respective initial discrete measurement, measurement sequence and/or developing the subsequent measurement result from a corresponding discrete measurement, or subsequent measurement sequence.

9. The method according to claim 8, wherein the initial measurement result is an average over the respective initial measurement sequence and/or wherein the subsequent measurement value is an average over the corresponding subsequent measurement sequence.

10. The method according to claim 8, wherein the initial measurement result is an initial rate of change for the initial measurement sequence, and wherein the subsequent measurement value is a subsequent rate of change for the corresponding subsequent measurement sequence.

11. The method according to claim 1, wherein the concentrations of the analyte contained in the primary and secondary solutions differ by at least a factor of 2, at least a factor of 5, at least a factor of 10, at least a factor of 20, at least a factor of 50, or at least a factor of 100.

12. The method according to claim 1, the method further comprising comparing the initial and subsequent measurement results, wherein the method further comprises determining a presence or absence of a clot in the measurement chamber based on the comparison of the initial and subsequent measurement results.

13. The method according to claim 12, wherein the presence or absence of a clot in the measurement chamber is determined by identifying a response to switching from a high analyte level in the primary solution to a low analyte level in the secondary solution or by identifying a response to switching from a low analyte level in the primary solution to a high analyte level in the secondary solution.

14. The method according to claim 12, wherein:

the determining the presence or absence of a clot in the measurement chamber based on the comparison of the initial and subsequent measurement results comprises comparing the difference between the initial and subsequent measurement results to a threshold; and the presence of a clot is determined if the difference between the initial and subsequent measurement results is above a threshold, and/or the absence of a clot is determined if the difference between the initial and subsequent measurement results is below the threshold.

15. A method of detecting a condition in a measurement chamber of a liquid sample analyzer, the liquid sample analyzer comprising one or more analyte sensors arranged for measuring a physical parameter of an analyte in a liquid sample in the measurement chamber and a liquid sensor configured to sense an amount of fluid in the measurement chamber, wherein detection is performed after conclusion of a rinsing procedure with a primary solution having a pre-determined primary composition with a primary concentration of the analyte, the method comprising:

(a) removing the primary solution from the measurement chamber;

(b) at least partly filling the measurement chamber with a secondary solution having a pre-determined secondary composition with a secondary concentration of the analyte, wherein the secondary concentration is different from the primary concentration, wherein the concentrations of the analyte contained in the primary and secondary solutions differ by at least a factor of 2, at least a factor of 5, at least a factor of 10, at least a factor of 20, at least a factor of 50, or at least a factor of 100;

(c) obtaining an initial measurement result by at least one of the one or more analyte sensors;

(d) flushing the measurement chamber with the secondary solution, and leaving the secondary solution in the measurement chamber; and (e) after a time delay from obtaining the initial measurement result, obtaining a subsequent measurement result by at least one of the one or more analyte sensors, wherein, during the step of at least partly filling the measurement chamber with the secondary solution, the liquid sensor monitors a filling amount of the secondary solution to just fill the measurement chamber with the secondary solution without completely flushing the measurement chamber.

16. The method according to claim 15, the method further comprising comparing the initial and subsequent measurement results and thereby determining a presence or absence of a clot in the measurement chamber based on the comparison of the initial and subsequent measurement results.

17. A liquid sample analyzer, the liquid sample analyzer comprising a measurement chamber with inlet and outlet ports for feeding and discharging a liquid sample to the measurement chamber, an analyte sensor facing the measurement chamber arranged for measuring a physical parameter of an analyte in a liquid sample in the measurement chamber, wherein the liquid sample analyzer is configured to detect a condition in the measurement chamber, wherein detection is performed after conclusion of a rinsing procedure with a primary solution having a pre-determined primary composition with a primary concentration of the analyte, and a signal processor configured for:

(a) receiving signals from the analyte sensor as an input, and (b) for performing a comparison of an initial measurement result and a subsequent measurement result based on that input, wherein the liquid sample analyzer is configured for:

(a) removing the primary solution from the measurement chamber;

(b) after removing the primary solution from the measurement chamber, at least partly filling the measurement chamber with a filling amount of a secondary solution having a pre-determined secondary composition with a secondary concentration of the analyte, wherein the filling amount of the secondary solution is metered to just fill the measurement chamber rather than to completely flush the measurement chamber with the secondary solution, wherein the secondary concentration is different from the primary concentration;

(c) obtaining the initial measurement result by the analyte sensor;

(d) flushing the measurement chamber with the secondary solution, and leaving the secondary solution in the measurement chamber;

(e) after a time delay from obtaining the initial measurement result, obtaining the subsequent measurement result by the analyte sensor; and (f) determining whether to feed the liquid sample through the measurement chamber, based on the comparison of the initial and subsequent measurement results, to thereby measure the physical parameter of the analyte in the liquid sample with the analyte sensor.

18. The liquid sample analyzer of claim 17, wherein the liquid sample analyzer is further configured for comparing the initial and subsequent measurement results.

* * * * *